United States Patent [19]

Rosenberg

[11] Patent Number: 4,578,355
[45] Date of Patent: Mar. 25, 1986

[54] PLASMID CLONING VECTOR PAS1

[75] Inventor: Martin Rosenberg, Malvern, Pa.

[73] Assignee: The United States of America as represented by the Department of Health and Human Services, Washington, D.C.

[21] Appl. No.: 457,352

[22] Filed: Jan. 12, 1983

[51] Int. Cl.[4] .................. C12N 1/00; C12N 15/00; C12P 21/00
[52] U.S. Cl. .................. 435/317; 435/172.3; 435/68; 935/11; 935/29
[58] Field of Search .............. 435/172.3, 317; 935/29, 935/23

[56] References Cited

PUBLICATIONS

Bernard et al., Gene, 5:59 (1979).
Kornberg, DNA Replication, W. H. Freeman & Comp. pp. 539–540, 1980.
Old et al., Principles of Gene Manipulation, 2d. Ed., University of California Press, pp. 35–38, 1981.
Backman, et al., Cell, vol. 13, pp. 65–71, 1978.
Shatzman et al., "A Plasmid Cloning Vector for Inducible Overproduction of Proteins in Bacterial Cells", Miami Symposium, Abstract, p. 98, Jan. 14, 1982.
Shimatake et al., Nature, vol. 292, pp. 128–132, 1981.
Su et al., J. Biol. Chem, vol. 257, vol. 15, pp. 9128–9134, 1982.
Lewin, Gene Expression—3, John Wiley, pp. 352–355 and 371, 1977.

Primary Examiner—Thomas G. Wiseman
Assistant Examiner—Jayme A. Huleatt
Attorney, Agent, or Firm—John S. Roberts, Jr.

[57] ABSTRACT

A plasmid cloning vector containing both transcriptional and translational regulatory sequences derived from the bacteriophage lambda genome was constructed to achieve high level expression of prokaryotic and eukaryotic genes. The system utilizes a plasmid vehicle carrying the strong, regulatable lambda promoter, $P_L$, and host lysogens into which this vector can be stably transformed. The lysogen synthesizes sufficient repressor (cI) to control $P_L$ expression and thereby stabilize plasmids which carry such a highly efficient promoter. Use of a temperature sensitive repressor permits simple, rapid induction of $P_L$ transcripts at any given time. Efficient transcription of essentially any coding sequence is assured by providing the phage lambda antitermination factor, N, and a site on the transcription unit for its utilization (Nut site). This pAS1 plasmid closely resembles the earlier constructed pKC30cII, also a regulatory protein which activates promoters for lysogenic development.

4 Claims, 2 Drawing Figures

PLASMID CLONING VECTOR PAS1

A plasmid cloning vector containing both transcriptional and translational regulatory sequences derived from the bacteriophage lambda genome was constructed to achieve high level expression of prokaryotic and eukaryotic genes.

The system utilizes a plasmid vehicle carrying the strong, regulatable lambda promoter, $P_L$, and host lysogens into which this vector can be stably transformed. The lysogen synthesizes sufficient repressor (cI) to control $P_L$ expression and thereby stabilize plasmids which carry such a highly efficient promoter. Use of a temperature sensitive repressor permits simple, rapid induction of $P_L$ transcripts at any given time. Efficient transcription of essentially any coding sequence is assured by providing the phage lambda antitermination factor, N, and a site on the transcription unit for its utilization (Nut site). This pAS1 plasmid closely resembles the earlier constructed pKC30cII. cII is a regulatory protein which activates promoters for lysogenic development.

This production of pAS1 was done by appropriately inserting into the $P_L$ transcription unit the ribosome binding site and initiation codon of the efficiently translated phage lambda cII gene. Immediately adjacent to the initiator ATG, there was engineered a unique cloning site which allows any coding sequence to be fused in frame directly to the cII start site. This system has been used to overproduce one prokaryotic (E. coli β-galactosidase) and one eukaryotic (SV40 small T antigen) protein. β-galactosidase is synthesized as 30-40% of cell protein and small T as >5% of cell protein after only a 60-90 minute induction.

EXPRESSION OF EUKARYOTIC GENES

Vector Construction

In order to extend the pKC30 system to the expression of genes lacking E. coli translational regulatory information, an efficient ribosome recognition and translation initiation site was engineered into the $P_L$ transcription unit. The site chosen was that of the efficiently translated λ phage gene, cII. The entire coding region of this gene was removed leaving only its initiator f-met codon and upstream regulatory sequences. Neither the sequence nor the position of any nucleotides in the ribosome binding region was altered. Instead, a restriction site for insertion of the desired gene was introduced immediately downstream from the ATG initiation codon. This was done by fusing the BamHI site of pBR322 directly to the cII ATG codon. This fusion retains the BamHI site and positions one side of the staggered cut immediately adjacent to the ATG codon permitting ready access to the cII translational regulatory information. The resulting vector, pAS1, allows direct fusion of any coding sequence (prokaryotic, eukaryotic, or synthetic) to the cII translational regulatory signal. Illustrative is the fusion of the lacZ gene shown post. Essentially, any gene can be adapted for insertion into the pAS1 vector and various examples are described below. Note that expression of genes cloned into pAS1 is controlled by temperature induction, exactly analogous to the pKC30 vector system.

Figure 2:
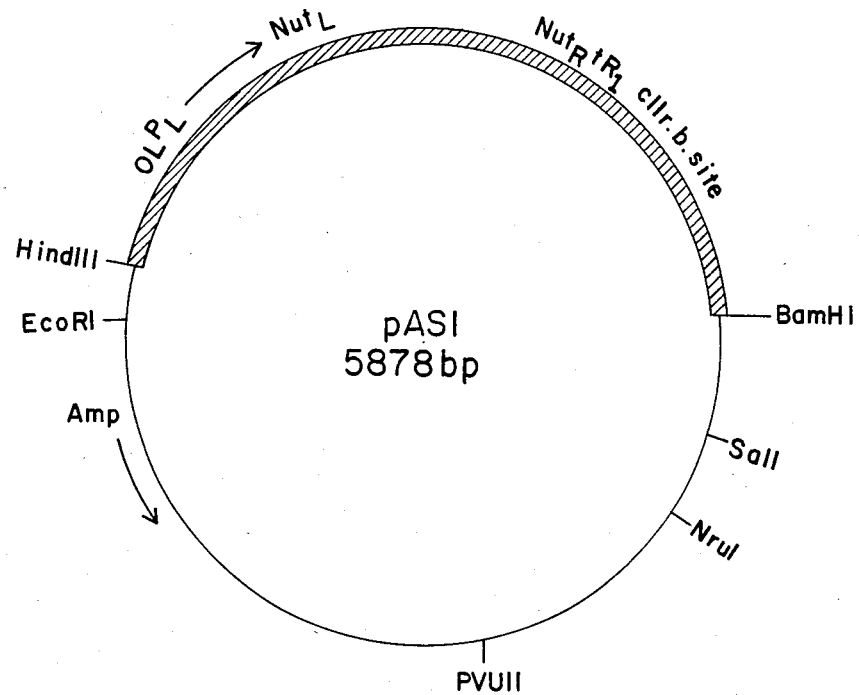
FIG. 2 is a partial genetic map of pAS1. Referring to the pKC30 system (derivative of pBR322) and pKC30cII system noted above and described at FIG. 1, the following is described as the production of the vector construction of pAS1 from its parent, pKC30.
Figure 2:
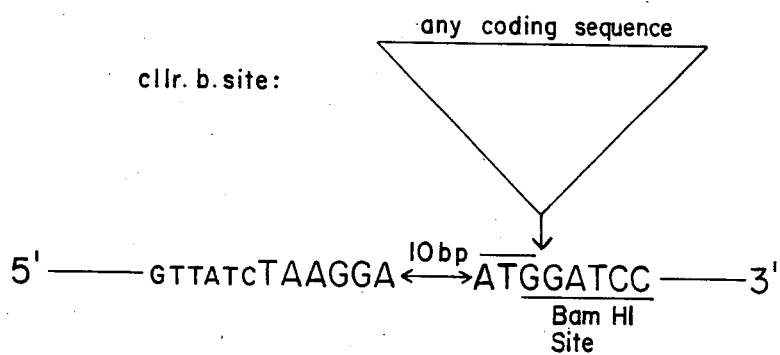

In other words, pAS1 is a plasmid vector capable of expressing a polypeptide comprising a plasmid having the $P_L$ promoter and Nut L site from pKC30 and, downstream of the Nut L site, the Nut R site, the tR1 site and the cII ribosome binding site including the cII translation initiation codon, from lambda DNA; immediately downstream of the cII ATG is a BamHI site, as illustrated in FIG. 2. The vector was constructed by inserting the lambda DNA between the HpaI and BamHI sites of pKC30. The lambda DNA had been previously mutationally altered such that the cII ribosome binding site could be fused to the BamHI site. The vector can be constructed from pKC30cII by cutting back the cII gene to the cII ATG, restricting the plasmid with BamHI, and religating the plasmid. The vector can also be constructed by similarly cutting back the cII gene from lambda DNA, attaching a BamHI linker, and inserting the Nut R—cII ATG fragment into pKC30.

Expression of lacZ in pAS1

In order to test the ability of the cII ribosome binding site to direct translation of another gene, there was initially fused the *E. coli* lacZ gene to the cII ATG initiation codon. This was accomplished by using a lacZ gene construction into which a unique BamHI restriction site had been engineered near the 5'-end of the gene. Direct ligation of this BamHI site to the BamHI site in pAS1 created the appropriate in frame fusion of lacZ to the cII ATG codon. In this vector lacZ expression is controlled entirely by the transcriptional and translational signals provided on pAS1. The pAS1 lacZ construction results in high level expression of β-galactosidase. After only one hour of temperature induction, β-galactosidase accounts for 30-40% of total cellular protein.

UTILITY STATEMENT

In addition to the utilities asserted in the abstract, it is noted that the present plasmid vector system may be utilized to achieve high level expression of particular phage regulatory protein which are normally found in only minute amounts in phage infected bacterial cells. The ease with which pAS1 vector may be used to fuse makes it commercially of great interest, particularly in regard to expressing polypeptides such as interferon, human growth hormone, and insulin.

PRIOR ART STATEMENT

Shatzman and Rosenberg, "A Plasmid Cloning Vector for Inducible Overproduction of Proteins in Bacterial Cells," Miami Symposium, Jan. 14, 1982, abstract, p. 98.

Shimatake and Rosenberg, "Purified λ Regulatory Proten cII Positively Activates Promoters for Lysogenic Development," *Nature*, Vol. 292, No. 5819, pp. 128-132, July 9, 1981.

Lewin, *Gene Expression*-3, John Wiley, 1977, Chapter 4 "Phage Lambda Infective Pathways," especially page 352 lysogeny and pages 355, 371 on turn off of repressor and cII gene.

Kornberg, *DNA Replication*, W. H. Freeman and Company, 1980, pp. 539-540, λ Temperate Phages.

Backman et al., "Maximizing Gene Expression on a Plasmid Using Recombination in Vitro," *Cell*, 13:65-71, January 1978—background information on ribosome binding sites (rbs).

Old et al., *Principles of Gene Manipulation*, 2d ed., University of California Press, 1981, pages 35+, re pBR322.

SOURCE

The description and production of the parent cII gene is described fully in the *Nature* article above (1981).

The conversion from cII to pAS1 is described in the present invention and pAS1 was deposited in ATCC, Rockville, Md., on Jan. 10, 1983, under Accession No. 39262.

ADAPTING pKC30 FOR THE EXPRESSION OF EUKARYOTIC GENES AND THE CHANGEOVER TO pAS1

Figure 1:
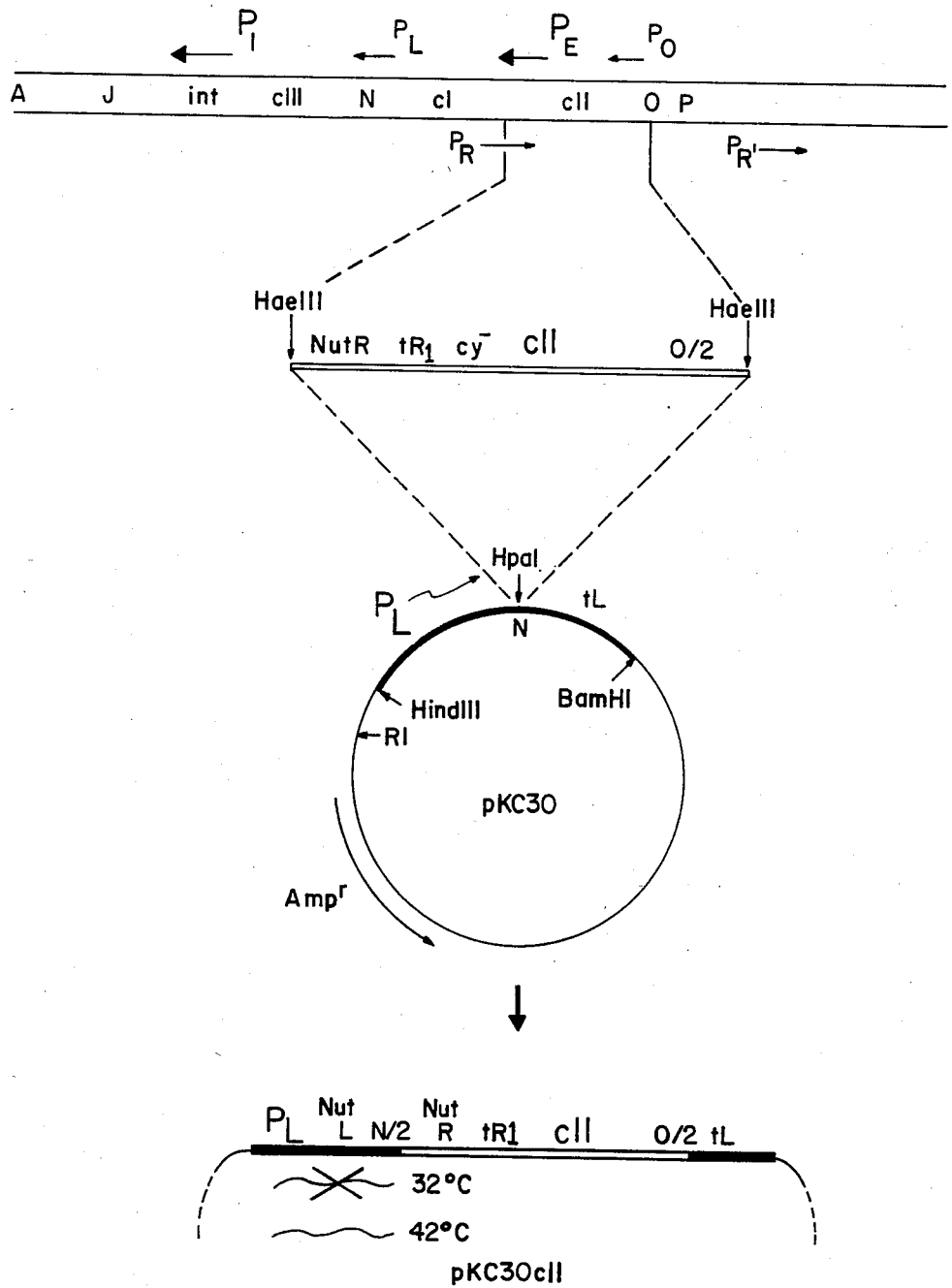
FIG. 1 is a partial genetic map of λ DNA, pKC30 and pKC30cII. The locations of the positively regulated promoters, $P_E$ and $P_1$, are indicated. These promoters are responsible for the coordinate expression of the phage lysogenic functions, repressor (cI) and integrase (int), respectively. Other major promoters are also shown ($P_R$, $P_L$, $P_O$, $P_R$). Expanded below is the region encompassed by a 1,300-bp HaeIII DNA restriction fragment, which contains the cII gene and several other previously characterized phage regulatory sites. The bottom portion of the figure is a diagram of the construction of the plasmid vector which overproduces cII protein (pKC30cII). The HaeIII restriction fragment was inserted into the single HpaI restriction site which occurs on the plasmid pKC30. This fragment contains the proposed site of recognition for the antitermination function N (NutR), the rho-dependent transcription termination site (tR1), the $P_E$ promoter mutation cy3048 (cy−), the cII coding region and the amino-terminal half of the O gene (O/2). The pKC30 plasmid is a derivative of plasmid pBR322 which contains a HindIII-BamHI restriction fragment derived from phage λ inserted between the HindIII and BamHI restriction sites within the tetracycline gene of pBR322. The λ insert contains the promoter signal, $P_L$, another proposed site of N recognition (NutL), the N gene and the strong rho-dependent transcription termination signal, tL. The HpaI restriction site occurs within the N gene coding region. Purified HaeII fragment (0.1 pmol) and HpaI-cleaved pKC30 plasmid (0.1 pmol) were blunt-end ligated at 15° C. for 14 h and recleaved with HpaI after ligation. This DNA was used to transform a λ lysogen carrying a temperature-sensitive mutation (cI857) in its repressor gene. Amp$^r$ recombinants were obtained and screened by size and restriction for the presence of the insert. Recombinants were obtained carrying the insert in both possible orientations. Note that the final pKC30cII construction contained the transcription regulatory sites, NutL, NutR and tR1, preceding the cII gene. Preliminary studies indicated that high-level protein expression required that the lysogen carry a functional N gene which was induced by temperature. This N gene product presumably functions at the Nut sites to antiterminate transcription at tR1.

The plasmid constructed for the expression of genes which do not normally carry regulatory signals for their translation in bacteria is shown in FIG. 2. This vector, pAS1, is related to pKC30cII except that all λ sequences downstream of the cII initiation codon have been deleted. The BamHI site of pBR322 is now fused directly to the cII ATG (FIG. 1). This fusion retains the BamHI site and positions one side of the staggered cut immediately adjacent to the ATG codon permitting ready access to the cII translational regulatory information. Eukaryotic and/or synthetic genes can be adapted and fused to this translation initiation signal. It is most important that all fusions between the gene coding sequence and the cII initiation codon maintain the correct translation reading frame. Below, procedures are described for inserting genes into the pAS1 vector. Note that all cloning experiments with pAS1, like those for pKC30, are carried out in a cI+ lysogen in order to maximize stability of the vector. Expression of the cloned gene takes place in the cI$^{ts}$ lysogen using procedures identical to those described above for pKC30.

CLONING AND EXPRESSION OF GENES IN pAS1

Direct Insertion At The BamHI Site

The genes which can be fused directly to the cII initiation codon are those which contain a BamHI, BglII, Sau3A or BclI restriction site at or near their own initiation codon. The necessary restriction site may occur naturally within the gene or be engineered into the gene by recombinant or synthetic techniques. Standard procedures may be used for the cloning, for clone analysis and expression.

Two genes have been cloned and expressed in pAS1 using this technique, the β-galactosidase gene (lacZ) of *E. coli* and the metallothionein II gene from monkey. The lacZ gene was engineered to contain a unique BamHI site near its 5' end, whereas the metallothionein gene naturally contained a BamHI site at its 2nd amino acid codon. In both cases direct BamHI ligation of the gene into pAS1 appropriately positioned the coding sequence in frame with the cII ATG codon. Expression of both genes was controlled entirely by transcriptional and translational signals provided on pAS1. The pAS1 lacZ construction results in high-level expression of β-galactosidase. Similar results were obtained with the monkey metallothionein gene.

PARTICULARITY FACTORS IN pAS1 ANTITERMINATION

N+Nut antitermination system, present in both the cII and pAS1, is a system for achieving high level expression of cII protein. cII production was found to be 8-10 times higher in lysogens which provided N as opposed to those which did not. More recent experiments indicate that the N+Nut system leads to increased expression of other genes cloned into pKC30 which do not have terminator signals preceding them.

The phrase "overproduction of the phage regulatory protein cII" is designed to bring out and emphasize that under ordinary conditions cII is not produced in transcriptional activation in amounts necessary to obtain the protein in sufficient amounts to allow for its purification and biochemical analysis. The cloning of the cII gene onto a multicopy plasmid vector requires an efficient transcriptional unit of which the N+Nut is a portion of that unit which is most important. Also important is the lysogen host which adds by a factor of 8-10 the amount of bacterial lysogens utilized as compared to the lack of lysogen host.

One advantage of this sytem is that a lysogen carrying a temperature sensitive mutation in the cI gene directed transcription can be activated at any time. Induction is accomplished by simply raising the temperature of the cell culture from 32° to 42° C. Thus, cells carrying the vector can be grown to high density at 32° C. without expression of the clone gene and subsequently induced at 42° C. to synthesize the product.

A further advantage of the N+Nut system is that the N expression removes transcriptional polarity, thereby alleviating termination within the $P_L$ transcription unit. This antitermination effect was particularly important for the expression of cII since a transcription termination signal, tR1, positioned immediately upstream of the cII coding region, would interfere.

Additionally, phage λ with promoters and anti-termination factors causes the effect in *E. coli* to keep the system lysogenic; i.e., bearing a lysogenic host.

EXAMPLE 1-A

Expression of SV40 Small t Antigen

Unlike the lacZ construction noted ante in this invention, most genes do not contain the restriction information necessary for their direct insertion into the BamHI site of pAS1. Thus, it was additionally necessary to provide greater flexibility for inserting DNA fragments into the vector. This was accomplished by converting the BamHI site of pAS1 into a blunt-ended cloning site. The four base 5'-overhanging end of the BamHI cleavage site can be removed using mung bean nuclease, thereby creating a blunt-end cloning site immediately adjacent to the cII initiation codon. Any gene containing any restriction site properly positioned at or near its 5'-end can now be inserted into this vehicle. Blunt-ended fragments can be inserted directly, whereas other restriction fragments must first be made blunt-ended. This is accomplished by either removing the 5' and 3'-overhanging ends with mung bean nuclease (as above) or "filling-in" the 5'-overhanging ends with DNA polymerase. Of course, this procedure still limits the use of pAS1 to those genes which contain appropriate restriction information near their 5'-termini. In order to make the pAS1 system generally applicable to the expression of any gene, a procedure was developed which allows precise placement of a new restriction site at the second codon (or any other codon) of any gene. Creation of this site permits fusion of the gene in-frame to the cII initiation codon of pAS1.

EXAMPLE 1-B

The small t antigen gene of SV40 does not contain an appropriate restriction site at its 5'-end. Using Ba131 exonucleolytic digestion from an upstream restriction site, the first base (G) of the second codon of the small t gene (ATG GAT . . . ) was fused to an upstream, filled-in AvaI restriction site ( . . . CCCGA).

The fusion, ( . . . CCCGAGAT . . . ) recreated the AvaI site precisely at the second codon of the small t gene. Restriction of this vector with AvaI followed by mung bean nuclease digestion produces a blunt-end which was fused in-frame to the blunt-ended BamHI site of pAS1. The resulting vector, pAS1t, expresses authentic SV40 small t antigen entirely from phage regulatory signals. After only a 60-minute induction period, small t antigen represents some 10% of the total cellular protein. Moreover, $^{35}$S-pulse labeling experiments indicate that small t is the major product being synthesized in these bacteria after temperature induction.

I claim:

1. pAS-1 as shown in a genetic map in FIG. 2A.

2. pAS1 plasmid vector as deposited in ATCC under Accession No. 39262.

3. The plasmid of claim 1 as defined by said genetic map and described by the following coding sequence of amino acids at the BamHI site

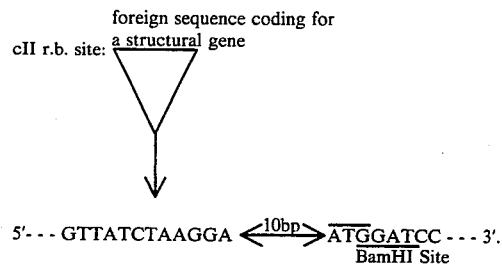

4. A plasmid vector capable of expressing a polypeptide comprising a plasmid containing in sequence a $P_L$ promoter and a Nut L site from pKC30; and downstream from said Nut L site is a Nut R site, a tR1 site, a cII ribosome binding site including a cII translation initiation codon from λ DNA, and a BamHI site.

* * * * *